United States Patent
Morinaga et al.

(10) Patent No.: US 9,671,480 B2
(45) Date of Patent: Jun. 6, 2017

(54) MAGNETIC RESONANCE IMAGING APPARATUS

(71) Applicants: Mayumi Morinaga, Sakai (JP); Kazuhiro Sueoka, Nasushiobara (JP)

(72) Inventors: Mayumi Morinaga, Sakai (JP); Kazuhiro Sueoka, Nasushiobara (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 1196 days.

(21) Appl. No.: 13/728,158

(22) Filed: Dec. 27, 2012

(65) Prior Publication Data

US 2013/0141097 A1 Jun. 6, 2013

Related U.S. Application Data

(63) Continuation of application No. PCT/JP2012/063943, filed on May 30, 2012.

(30) Foreign Application Priority Data

May 31, 2011 (JP) .................. 2011-122561

(51) Int. Cl.
*G01R 33/48* (2006.01)
*G01R 33/483* (2006.01)
(Continued)

(52) U.S. Cl.
CPC .......... *G01R 33/48* (2013.01); *A61B 5/055* (2013.01); *G01R 33/4835* (2013.01); *G01R 33/543* (2013.01)

(58) Field of Classification Search
CPC .... A61B 5/055; G01R 33/48; G01R 33/4835; G01R 33/543; G01R 33/4833; G01R 33/483; G01R 33/4836
See application file for complete search history.

(56) References Cited

U.S. PATENT DOCUMENTS

| | | | |
|---|---|---|---|
| 2003/0139660 A1* | 7/2003 | Tatebayashi | A61B 5/055 600/407 |
| 2006/0122487 A1* | 6/2006 | Tatebayashi | A61B 5/055 600/410 |

(Continued)

FOREIGN PATENT DOCUMENTS

| | | |
|---|---|---|
| JP | 4-35648 | 2/1992 |
| JP | 6-90926 | 4/1994 |

(Continued)

OTHER PUBLICATIONS

JP Office Action dated Apr. 19, 2016 in JP 2012-123605.

(Continued)

*Primary Examiner* — Melissa Koval
*Assistant Examiner* — Rishi Patel
(74) *Attorney, Agent, or Firm* — Nixon & Vanderhye P.C.

(57) ABSTRACT

The MRI apparatus includes an image generating unit, an area setting unit, a slice condition determining unit and an imaging executing unit. The image generating unit images an object at a predetermined imaging position, and generates an image for positioning. The area setting unit sets a slab area and a slice area on a basis of a recommended value that is stored in a storage and corresponds to the predetermined imaging position, and to display the set slab area and the set slice area on the image for positioning, the storage storing the recommended value of a parameter concerning a slice condition for each of a plurality of imaging positions. The slice condition determining unit determines the slice condition on a basis of the slice area. The imaging executing unit executes an imaging of the slab area in accordance with the determined slice condition.

10 Claims, 10 Drawing Sheets

(51) Int. Cl.
*A61B 5/055* (2006.01)
*G01R 33/54* (2006.01)

(56) References Cited

U.S. PATENT DOCUMENTS

| | | | |
|---|---|---|---|
| 2008/0214926 A1* | 9/2008 | Fukuta | ................. A61B 5/7425 600/410 |
| 2011/0074418 A1 | 3/2011 | Wu et al. | |
| 2011/0187365 A1* | 8/2011 | Ohmure | ................. G01R 33/48 324/309 |
| 2012/0093385 A1 | 4/2012 | Yokosawa et al. | |

FOREIGN PATENT DOCUMENTS

| | | |
|---|---|---|
| JP | 2003-290172 | 10/2003 |
| JP | 2006-255189 | 9/2006 |
| WO | WO 2009/151041 | 12/2009 |
| WO | WO 2010/150783 A1 | 12/2010 |

OTHER PUBLICATIONS

English Translation of International Preliminary Report on Patentability issued Dec. 2, 2013 for Application No. PCT/JP2012/063943.
International Search Report for PCT/JP2012/063943, mailed Jun. 26, 2012.

\* cited by examiner

| SEQUENCE | IMAGING POSITION (SITE) | IMAGES FOR POSITIONING (CROSS-SECTION) | PARAMETERS CONCERNING SLICE CONDITION | | | | CHANGE PRIORITY PARAMETER |
|---|---|---|---|---|---|---|---|
| | | | ANGULAR INFORMATION | SLICE THICKNESS | SLICE INTERVAL | THE NUMBER OF SLICES | |
| FE | HEAD PORTION | AX | 10 | 10 | 2 | 3 | SLICE INTERVAL |
| | | SG | 15 | 8 | 1 | 3 | SLICE THICKNESS |
| | | CO | 15 | 15 | 2 | – | THE NUMBER OF SLICES |
| SE | CHEST PORTION | AX | 10 | 10 | 2 | – | – |
| | | SG | 15 | 8 | 1 | – | – |
| | | CO | 15 | 15 | 2 | – | – |

| SEQUENCE | IMAGING POSITION (SITE) | IMAGES FOR POSITIONING (CROSS-SECTION) | PARAMETERS CONCERNING SLICE CONDITION ||||
|---|---|---|---|---|---|---|
| | | | ANGULAR INFORMATION | SLICE THICKNESS | SLICE INTERVAL | THE NUMBER OF SLICES |
| FE | HEAD PORTION | AX | 10 | 10 | 2 | MAXIMUM VALUE |
| | | SG | 15 | 8 | 1 | MAXIMUM VALUE |
| | | CO | 15 | 15 | 2 | MAXIMUM VALUE |
| SE | CHEST PORTION | AX | 10 | 10 | 2 | MAXIMUM VALUE |
| | | SG | 15 | 8 | 1 | MAXIMUM VALUE |
| | | CO | 15 | 15 | 2 | MAXIMUM VALUE |

MAGNETIC RESONANCE IMAGING APPARATUS

CROSS-REFERENCE TO RELATED APPLICATION

This application is a Continuation Application of No. PCT/JP2012/063943, filed on May 30, 2012, and the PCT application is based upon and claims the benefit of priority from Japanese Patent Application No. 2011-122561, filed on May 31, 2011, the entire contents of which are incorporated herein by reference.

FIELD

The present embodiment as an aspect of the present invention relates to a magnetic resonance imaging apparatus configured to set a slab area to an object and then image that slab area.

BACKGROUND

A conventionally known technique for diagnosing, for example, a hernia of lumbar intervertebral disc using a magnetic resonance imaging (MRI) apparatus executes cross-sectional imaging concerning the hernia along the intervertebral disc. A technique called multi-angle and multi-scan method is normally used for such cross-sectional imaging along the intervertebral disc. In the case of imaging according to this technique, for a preparatory stage thereof, a sagittal image of vertebrae of an object is obtained in advance as an image for positioning, and a large number of slices (slice areas) are set on the sagittal image. Scanning of the set slices is executed according to the multi-angle and multi-scan method, whereby tomographic images of the set slices are obtained.

In clinical photographing of a hernia of intervertebral disc, a plurality of slice areas that are adjacent and substantially parallel to each other along the intervertebral disc are further set in order to observe upward/downward development of the hernia of intervertebral disc. Note that a group of such a plurality of slice areas that are adjacent and substantially parallel to each other is hereinafter referred to as slab area. An operator sets in advance a slice condition including a slice thickness, a slice interval (gap), and the number of slices of each slice area in the slab area, and sets a position of the slab area using an image for positioning.

In the case where a plurality of slab areas are set on an imaging condition editing screen, in principle, if one slice condition is set, the set slice condition is applied to the plurality of slab areas.

In a disclosed MRI apparatus, a slab area is set on the basis of two points that are specified by an operator on an image for positioning, and in the set slab area, slice areas according to a slice condition specified in advance are adjacently placed substantially parallel to each other.

The conventional art includes the case where a plurality of slab areas are set at one imaging position (site), that is, the case where a second slab area is additionally set after setting of a first slab area. In this case, an operator's operation is complicated if the operator desires to alter a slice condition in the second slab area from a slice condition that are set in advance for the setting of the first slab area. Specifically, if the operator desires to alter the slice condition in the second slab area from the slice condition that was set in advance for the setting of the first slab area, the operator needs to return to the imaging condition editing screen and make an operation to alter the slice condition, after the setting of the first slab area.

The conventional art also includes the case where a slab area is set for each imaging position, that is, the case where a slab area of a second imaging position is additionally set after setting of a slab area of a first imaging position. Similarly in this case, the operator's operation is complicated. Specifically, if the operator desires to alter the slice conditions in the slab area of the second imaging position from the slice conditions that are set in advance for the setting of the slab area of the first imaging position, because slice conditions different for each imaging position are not able to be set, the operator needs to return to the imaging condition editing screen and make an operation to alter the slice conditions, after the setting of the slab area of the first imaging position.

In addition, according to the conventional art, in the case where a plurality of slice areas according to a slice condition are not able to fall within a slab area set on an image for positioning, the operator needs to make an operation of, for example, changing the set slab area, and this puts a burden on the operator.

BRIEF DESCRIPTION OF THE DRAWINGS

In accompanying drawings.

DETAILED DESCRIPTION

A magnetic resonance imaging (MRI) apparatus according to the present embodiment is described with reference to the attached drawings.

The present embodiments provide an MRI apparatus including: an image generating unit configured to image an object at a predetermined imaging position, and to generate an image for positioning; an area setting unit configured to set a slab area and a slice area on a basis of a recommended value that is stored in a storage and corresponds to the predetermined imaging position, and to display the set slab area and the set slice area on the image for positioning, the storage storing the recommended value of a parameter concerning a slice condition for each of a plurality of imaging positions; a slice condition determining unit configured to determine the slice condition on a basis of the slice area; and an imaging executing unit configured to execute an imaging of the slab area in accordance with the determined slice condition.

The present embodiments provide an MRI apparatus including: an image generating unit configured to image an object at a predetermined imaging position, and to generate an image for positioning; a temporary setting unit configured to temporarily set values of a plurality of parameters concerning a slice condition for each of a plurality of imaging positions; a slab setting unit configured to set a slab area on the image for positioning; a final setting unit configured to preferentially change, in a case where a plurality of slice areas according to the plurality of parameters are placed, if the plurality of slice areas do not fall within the slab area, a temporary set value of a change priority parameter that is stored in a storage and corresponds to the predetermined imaging position, such that the plurality of slice areas fall within the slab area, and to set the partially changed slice condition, the storage storing the change priority parameter for each imaging position; and an imaging executing unit configured to execute an imaging of the slab area in accordance with the finally set slice condition.

The present embodiments provide an MRI apparatus including: an image generating unit configured to image an object at a predetermined imaging position, and to generate an image for positioning; a temporary setting unit configured to temporarily set values of a plurality of parameters concerning a slice condition for each of a plurality of imaging positions; a slab setting unit configured to set a slab area on the image for positioning; a final setting unit configured to change, in a case where a plurality of slice areas according to the plurality of parameters are placed, if the plurality of slice areas do not fall within the slab area, a temporary set value of a number of slices, which is one of the plurality of parameters, such that the plurality of slice areas fall within the slab area, and to set the slice condition; and an imaging executing unit configured to execute an imaging of the slab area in accordance with the finally set slice condition.

First Embodiment

Figure 1:
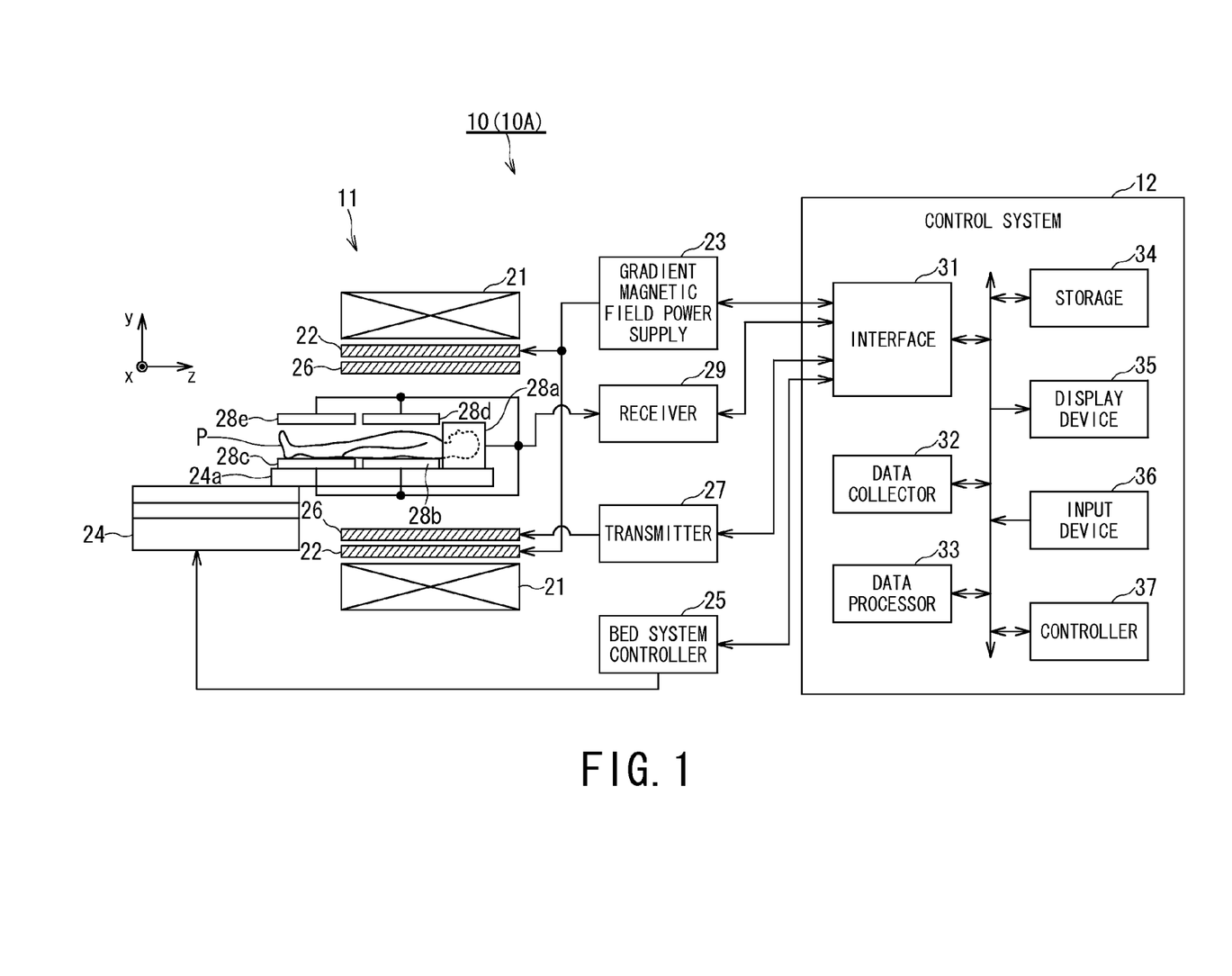
FIG. 1 is a schematic diagram showing a hardware configuration of an MRI apparatus according to a first embodiment.

FIG. 1 is a schematic diagram showing a hardware configuration of an MRI apparatus according to a first embodiment.

FIG. 1 shows an MRI apparatus 10 according to a first embodiment configured to image an object (patient) P. The MRI apparatus 10 roughly includes an imaging system 11 and a control system 12.

The imaging system 11 includes a static magnetic field magnet 21, a gradient magnetic field coil 22, a gradient magnetic field power supply 23, a bed system 24, a bed system controller 25, a transmitter coil 26, a transmitter 27, receiver coils 28a to 28e, and a receiver 29.

The static magnetic field magnet 21 is formed into a hollow cylindrical shape at the outermost portion of a gantry (not shown), and generates a uniform static magnetic field in internal space thereof. For example, a permanent magnet and a superconducting magnet are used as the static magnetic field magnet 21.

The gradient magnetic field coil 22 is formed into a hollow cylindrical shape, and is placed on the inner side of the static magnetic field magnet 21. The gradient magnetic field coil 22 is formed of a combination of three coils respectively corresponding to axes of x, y, and z orthogonal to one other. These three coils individually receive current supply from the gradient magnetic field power supply 23 to be described later, and generate gradient magnetic fields having magnetic field intensities that respectively vary along the axes of x, y, and z. Note that the z-axis direction is defined as the same direction as the static magnetic field.

Here, the gradient magnetic fields of the axes of x, y, and z that are generated by the gradient magnetic field coil 22 respectively correspond to, for example, a gradient magnetic field for reading out Gr, a gradient magnetic field for phase encoding Ge, and a gradient magnetic field for slice selection Gs. The gradient magnetic field for reading out Gr is used to vary the frequency of nuclear magnetic resonance (NMR) signals in accordance with a spatial position. The gradient magnetic field for phase encoding Ge is used to vary the phase of NMR signals in accordance with a spatial position. The gradient magnetic field for slice selection Gs is used to appropriately determine cross-sections for imaging.

The gradient magnetic field power supply 23 supplies current to the gradient magnetic field coil 22 on the basis of pulse sequence execution data sent from the control system 12.

The bed system 24 includes a table-top 24a on which the object P is to be placed. Under control of the bed system controller 25 to be described later, the bed system 24 inserts the table-top 24a into the hollow portion (imaging space) formed by the gradient magnetic field coil 22 in the state where the object P is placed on the bed system 24. Normally, the bed system 24 is installed such that the longitudinal direction thereof is parallel to the central axis of the static magnetic field magnet 21.

The bed system controller 25 drives the bed system 24 to move the table-top 24a in the longitudinal direction and the horizontal direction.

The transmitter coil 26 is placed on the inner side of the gradient magnetic field coil 22, and receives supply of high-frequency pulses from the transmitter 27 to generate a high-frequency magnetic field.

The transmitter 27 transmits, to the transmitter coil 26, high-frequency pulses corresponding to the Larmor frequency on the basis of pulse sequence execution data sent from the control system 12.

The receiver coils 28a to 28e are placed on the inner side of the gradient magnetic field coil 22, and receive NMR signals that are emitted from the object P due to an influence of the high-frequency magnetic field. Here, the receiver coils 28a to 28e are array coils each including a plurality of element coils configured to receive magnetic resonance signals emitted from the object P. When the respective element coils receive NMR signals, the receiver coils 28a to 28e output the received NMR signals to the receiver 29.

The receiver coil 28a is a coil for head portion attached to the head portion of the object P. The receiver coils 28b and 28c are coils for spine placed between the back of the object P and the table-top 24a. The receiver coils 28d and 28e are coils for abdomen attached on the abdomen side of the object P.

The receiver 29 generates NMR signal data based on the NMR signals outputted from the receiver coils 28a to 28e, on the basis of pulse sequence execution data sent from the control system 12. After the generation of the NMR signal data, the receiver 29 transmits the generated NMR signal data to the control system 12.

Note that the receiver 29 includes a plurality of receiving channels for receiving the NMR signals outputted from the plurality of element coils included in the receiver coils 28a to 28e. Then, in the case where the control system 12 reports which element coil is to be used for imaging, the receiver 29 assigns a receiving channel to the reported element coil such that the NMR signals outputted from the reported element coil are received.

The control system 12 performs overall control of the MRI apparatus 10, data collection, image reconstruction, and the like. The control system 12 includes an interface 31, a data collector 32, a data processor 33, a storage 34, a display device 35, an input device 36, and a controller 37.

The interface 31 is connected to the gradient magnetic field power supply 23, the bed system controller 25, the transmitter 27, and the receiver 29, and controls input/output of signals exchanged between these connected units and the control system 12.

The data collector 32 collects the NMR signal data transmitted from the receiver 29, with the intermediation of the interface 31. After the collection of the NMR signal data, the data collector 32 causes the storage 34 to store the collected NMR signal data.

The data processor 33 performs post-processing, that is, reconstruction processing such as Fourier transform on the NMR signal data stored in the storage 34, to thereby generate spectrum data or image data of a desired nuclear spin in the object P. In addition, in the case where an imaging for positioning is executed, the data processor 33 generates, for each element coil, profile data indicating the distribution of the NMR signals in the arrangement direction of the element coils, on the basis of the NMR signals received by the plurality of element coils included in the receiver coils 28a to 28e. Then, the data processor 33 stores the pieces of generated data into the storage 34.

Figure 2:
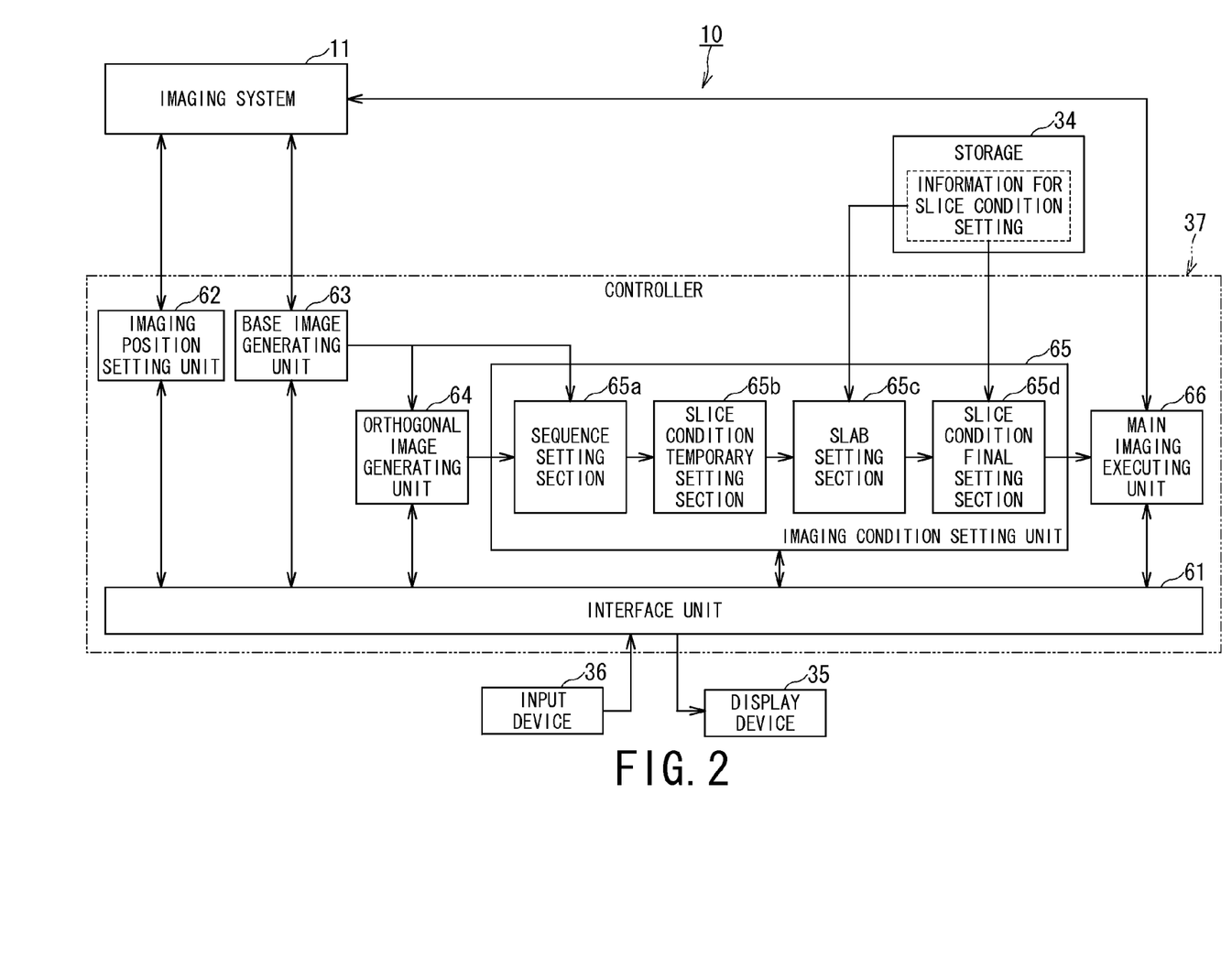
FIG. 2 is a block diagram showing a function of the MRI apparatus according to the first embodiment.

The storage 34 stores, for each object P, the NMR signal data collected by the data collector 32 and the image data and the like generated by the data processor 33. The storage 34 also stores information for slice condition setting as shown in FIG. 2.

The display device 35 displays various pieces of information such as the spectrum data and/or the image data generated by the data processor 33. A display device such as a liquid crystal display is able to be used as the display device 35.

The input device 36 receives various operations and information inputs from an operator. A pointing device such as a mouse and a trackball, a selection device such as a mode selector switch, or an input device such as a keyboard is able to be used as the input device 36 as appropriate.

The controller 37 includes a central processing unit (CPU), a memory, and the like, which are not shown in the drawings, and controls the functional units described above to thereby comprehensively control the MRI apparatus 10.

FIG. 2 is a block diagram showing a function of the MRI apparatus 10 according to the first embodiment.

As shown in FIG. 2, when the CPU of the controller 37 executes a program, the MRI apparatus 10 functions as an interface unit 61, an imaging position setting unit 62, a base image generating unit 63, an orthogonal image generating unit 64, an imaging condition setting unit 65, and a main imaging executing unit 66. Note that description is given below assuming that the components 61 to 66 of the MRI apparatus 10 are caused to function in the form of software, but a part or the entirety of the components 61 to 66 may be provided as a circuit in the MRI apparatus 10.

The interface unit 61 is an interface such as a graphical user interface (GUI) that mediates between: the components 62 to 66; and the display device 35 and the input device 36.

The imaging position setting unit 62 has a function of setting one or more imaging positions (sites) concerning the object P. For example, the imaging position setting unit 62 sets imaging position(s) on the basis of an input signal that is inputted by the operator using the input device 36 on an imaging condition editing screen. If a desired imaging position is set from among the plurality of imaging positions, the imaging condition setting unit 65 to be described later sets an imaging condition, including a sequence, a scanning condition and the like, corresponding to the set imaging position. That is, in the case where the imaging condition setting unit 65 to be described later sets the imaging condition, the imaging position is set prior to the setting of the imaging condition. In addition, for example, the imaging position setting unit 62 sets imaging position(s) through structure recognition of volume data that is obtained by volume scanning by the base image generating unit 63 to be described later. In addition, for example, the imaging position setting unit 62 sets imaging position(s) on the basis of: a coil element that receives NMR signals, among the receiver coils 28a to 28e, the coil element being set on the basis of an input signal that is inputted by the operator using the input device 36; and the entering direction (head first or feet first) of the object into the gantry. Description is given below of the case where the imaging position setting unit 62 sets a plurality of imaging positions concerning the object P.

Figure 3:
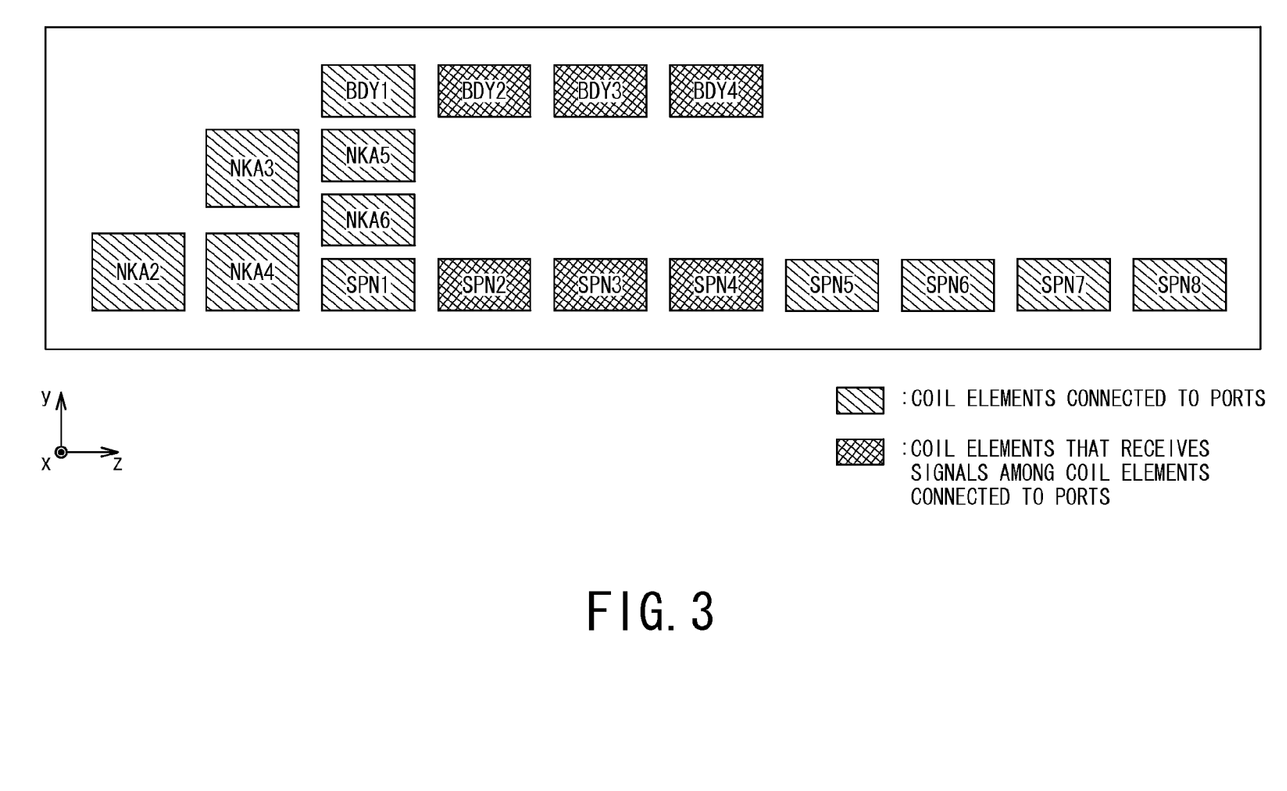
FIG. 3 is a diagram for expressing a coil element(s) that receives NMR signals, among receiver coils.

FIG. 3 is a diagram for expressing a coil element(s) that receives NMR signals, among the receiver coils 28.

The display device 35 displays a plurality of coil elements connected to a plurality of ports (not shown) provided to the table-top 24a. If the operator selects a coil element that receives NMR signals from among the plurality of coil elements connected to the plurality of ports, a state shown in FIG. 3 is obtained. In the example shown in FIG. 3, coil elements NKA2 to NKA6 of the coil for head portion 28a, coil elements SPN1 to SPN8 of the coils for spine 28b and 28c, and coil elements BDY1 to BDY4 of the coils for abdomen 28d and 28e, which are the receiver coils 28, are connected to the plurality of ports. Then, the operator selects the coil elements SPN2 to SPN4 and BDY2 to BDY4 that receive NMR signals from among the plurality of coil elements NKA2 to NKA6, SPN1 to SPN8, and BDY1 to BDY4 connected to the plurality of ports.

The imaging position setting unit 62 has a function of setting imaging positions of the object P on the basis of: the coil elements SPN2 to SPN4 and BDY2 to BDY4 (shown in FIG. 3) that receive NMR signals; and the entering direction of the object P into the gantry.

Returning to the description of FIG. 2, the base image generating unit 63 has a function of: controlling the operation of the imaging system 11 in accordance with an imaging condition for a preliminary imaging (which is an imaging for setting parameters of the imaging condition for a main imaging) prior to the main imaging; and thus executing imagings at the plurality of imaging positions set by the imaging position setting unit 62, to thereby generate respective base images which are cross-sectional images. Specifically, the base image generating unit 63 generates, as a base image, one of three orthogonal cross-sectional images, that is, an axial (AX) image, a sagittal (SG) image, and a coronal (CO) image. Description is given here assuming that the base image generating unit 63 generates the sagittal image as the base image. The sagittal image is displayed on the display device 35 with the intermediation of the interface unit 61.

The orthogonal image generating unit 64 has a function of generating orthogonal cross-sectional images taken along two cross-sections orthogonal to the base image, on the basis of the base image that is generated by the base image generating unit 63 for each imaging position. For example, the orthogonal image generating unit 64 reconstructs an axial image and a coronal image that are the rest of the three orthogonal cross-sectional images, on the basis of the sagittal image generated by the base image generating unit 63. The coronal image and the axial image are displayed on the display device 35 with the intermediation of the interface unit 61.

The imaging condition setting unit 65 includes a sequence setting section 65a, a slice condition temporary setting section 65b, a slab setting section 65c, and a slice condition final setting section 65d. The imaging condition setting unit 65 edits an imaging condition on the imaging condition editing screen.

The sequence setting section 65a has a function of setting a sequence of a main imaging, included in the imaging condition, on the basis of an input signal that is inputted by the operator using the input device 36 on the imaging condition editing screen.

The slice condition temporary setting section 65b has a function of temporarily setting values of a slice thickness, a slice interval (gap), the number of slices, and the like, which are parameters concerning the slice condition of a slice area (ROI: region of interest), included in the imaging condition, on the basis of an input signal that is inputted by the operator using the input device 36 on the imaging condition editing screen. The slice condition temporary setting section 65b displays the input signal from the input device 36 on the imaging condition editing screen, with the intermediation of the interface unit 61.

The slab setting section 65c has a function of setting angular information (oblique angle information) in the slice length direction of a slice area, which is a parameter concerning the slice condition of the slice area, on the basis of: the information for slice condition setting (shown in FIG. 6) stored in the storage 34; and the imaging positions set by the imaging position setting unit 62. The slab setting section 65c also has a function of setting a slab area on the image for positioning, on the basis of: an input signal that is inputted by the operator using the input device 36; and the set angular information. The slab area is formed into a rectangle, a parallelogram, and a rhombus, and description is given below assuming that the slab area is formed into a rectangle. The slab setting section 65c displays the input signal from the input device 36 on the imaging condition editing screen, with the intermediation of the interface unit 61. Note that the image for positioning may be a multi-planar reconstruction (MPR) image based on three orthogonal cross-sectional images.

Figure 4:
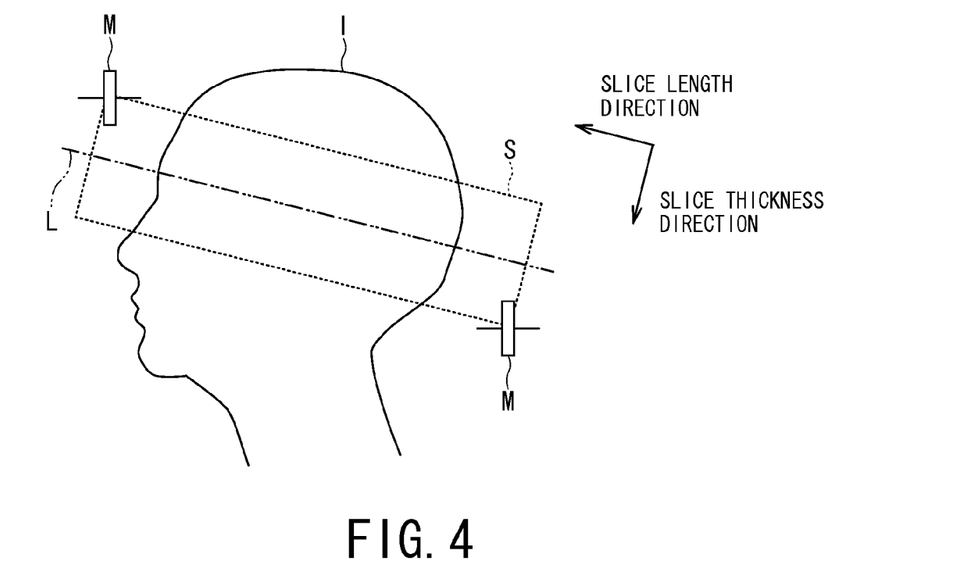
FIG. 4 is a diagram for expressing an example method of setting a slab area on a sagittal image.

FIG. 4 is a diagram for expressing an example method of setting a slab area on a sagittal image.

FIG. 4 shows: a sagittal image I serving as the image for positioning; markers M that are inputted from the input device 36 with the intermediation of the interface unit 61; a rectangular slab area S that is formed by the markers M and is based on angular information of slice areas; and a central line L in the slice thickness direction of the slab area S. The slab area S is set by the markers M at two opposed vertexes of a rectangle.

Returning to the description of FIG. 2, the slice condition final setting section 65d has a function of setting rectangular slice areas in the slab area set by the slab setting section 65c, on the basis of: the temporary set values of the parameters set by the slice condition temporary setting section 65b; and the angular information set by the slab setting section 65c.

If determining that all the slice areas according to the temporary set values of the parameters set by the slice condition temporary setting section 65b fall within the slab area, the slice condition final setting section 65d finally sets the temporary set values of the parameters without any change.

Figure 5:
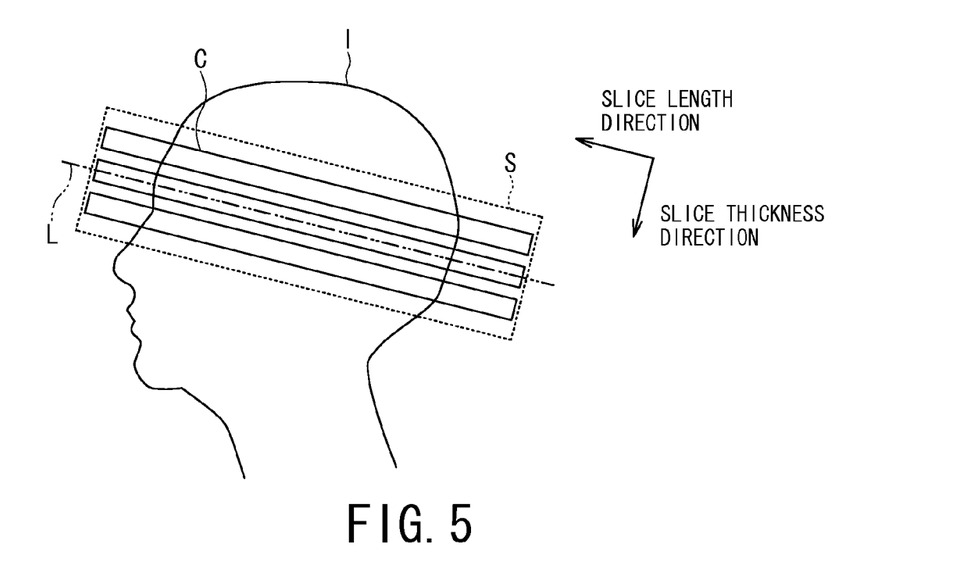
FIG. 5 is a diagram for expressing final setting of slice areas in a slab area on a sagittal image in the case where all the slice areas fall within the slab area.

FIG. 5 is a diagram for expressing final setting of slice areas in a slab area on a sagittal image in the case where all the slice areas fall within the slab area.

FIG. 5 shows: the sagittal image I serving as the image for positioning; the slab area S; the central line L; and three rectangular slice areas C based on angular information of the slice areas. The three slice areas C are placed in accordance with the temporary set values of the parameters set by the slice condition temporary setting section 65b so as to be, for example, parallel to the central line L and symmetrical with respect to the central line L. In the example shown in FIG. 5, all the three slice areas are able to fall within the slab area S. Note that the three slice areas C shown in FIG. 5 may be placed at regular intervals in the slice thickness direction within the slab area S, but the present embodiment is not limited thereto, and the three slice areas C shown in FIG. 5 may be placed at irregular intervals in the slice thickness direction within the slab area S.

On the other hand, if determining that at least one slice area according to the temporary set values of the parameters set by the slice condition temporary setting section 65b is not able to fall within the slab area, the slice condition final setting section 65d partially changes the temporary set values of the parameters in accordance with the information for slice condition setting stored in the storage 34, and finally sets the partially changed values.

Figure 6:
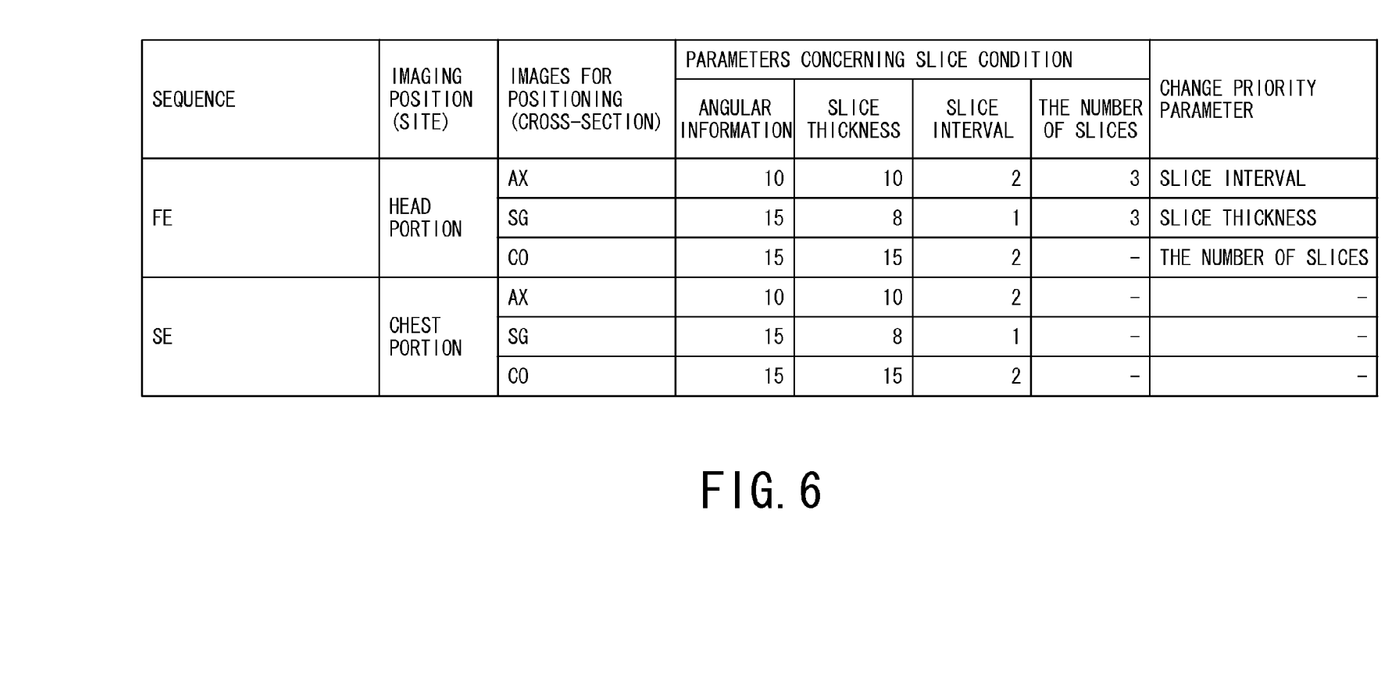
FIG. 6 is a table showing information for slice condition setting for setting a slice condition.

FIG. 6 is a table showing information for slice condition setting for setting a slice condition.

FIG. 6 shows the information for slice condition setting indicating: recommended values of a plurality of parameters included in the slice condition, for example, angular information, a slice thickness, a slice interval, and the number of slices, which are given for each sequence, for each imaging position (site), and for each cross-section of the three orthogonal cross-sectional images; and a change priority parameter among the plurality of parameters. Note that the information for slice condition setting may contain the recommended values of the parameters and the change priority parameter at least for each imaging position.

For example, it is discussed in FIG. 6 that the sagittal image is used as the image for positioning in the case of imaging a head portion according to a field echo (FE) method. In the case where at least one slice area is not able to fall within the slab area, that is, in the case where one of the values of the slice thickness, the slice interval, and the number of slices temporarily set by the slice condition temporary setting section 65b needs to be changed in order to enable the slice area to fall within the slab area, the slice condition final setting section 65d preferentially changes the temporary set value of the slice thickness as the change priority parameter, to its recommended value "8". Then, for example, it is discussed in FIG. 6 that the sagittal image is used as the image for positioning in the case of imaging a chest portion according to a spin echo (SE) method. Even in the case where one of the slice thickness, the slice interval, and the number of slices temporarily set by the slice condition temporary setting section 65b needs to be changed, the change priority parameter does not exist. In this case, the slice condition final setting section 65d may report, to the operator, that the slice condition need to be temporarily set again or that the slab area needs to be set again, or may automatically change the slab area such that all the slice areas fall within the slab area.

Figure 7A:
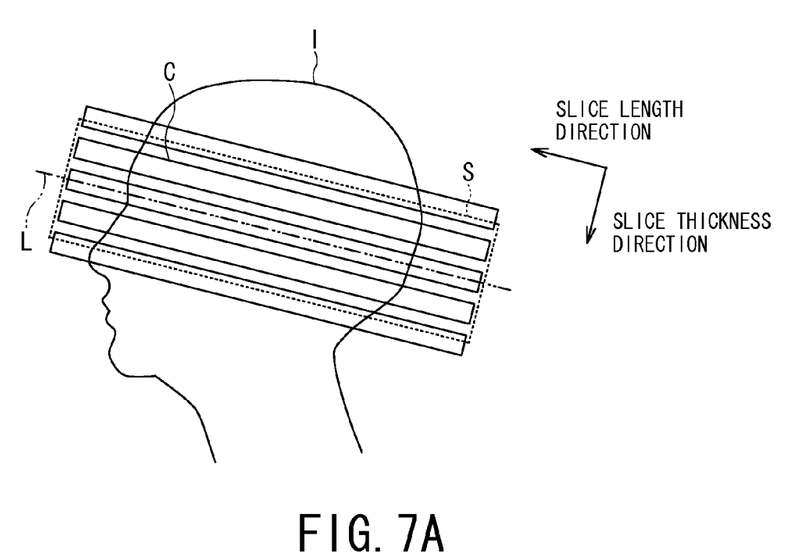
FIGS. 7A and 7B are diagrams for expressing final setting of slice areas in a slab area on a sagittal image in the case where at least one slice area is not able to fall within the slab area.
Figure 7B:
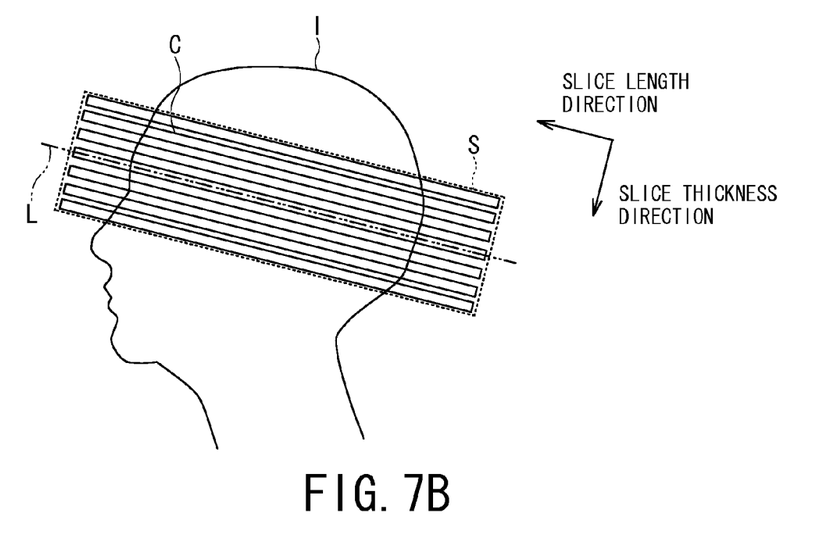

FIGS. 7A and 7B are diagrams for expressing final setting of slice areas in a slab area on a sagittal image in the case where at least one slice area is not able to fall within the slab area.

FIGS. 7A and 7B each show: the sagittal image I serving as the image for positioning; the slab area S; the central line L; and five rectangular slice areas C based on angular information of the slice areas. The seven slice areas C shown in FIG. 7A are placed in accordance with the temporary set values of the parameters set by the slice condition temporary setting section 65b so as to be parallel to the central line L and symmetrical with respect to the central line L. In the example shown in FIG. 7A, two slice areas are not able to fall within the slab area. Note that the seven slice areas C shown in FIGS. 7A and 7B may be placed at regular intervals in the slice thickness direction within the slab area S, but the present embodiment is not limited thereto, and the seven slice areas C shown in FIGS. 7A and 7B may be placed, for example, at irregular intervals in the slice thickness direction within the slab area S.

In the case shown in FIG. 7A, that is, in the case where at least one slice area is not able to fall within the slab area, the temporary set values of the parameters set by the slice condition temporary setting section 65b are partially changed in accordance with the information for slice condition setting shown in FIG. 6. For example, when the sagittal image is used as the image for positioning in the case of imaging a head portion according to an FE method, as shown in FIG. 7B, the slice condition final setting section 65d preferentially changes the temporary set value of the slice thickness as the change priority parameter, to its recommended value "8" such that the seven slice areas fall within the slab area.

Here, in the case where at least one slice area is not able to fall within the slab area even after any of the parameter of the slice condition is changed in accordance with the information for slice condition setting shown in FIG. 6, the slice condition final setting section 65d may report, to the operator, that the slice conditions need to be temporarily set again or that the slab area needs to be set again, or may automatically change the slab area such that all the slice areas fall within the slab area.

Returning to the description of FIG. 2, the main imaging executing unit 66 has a function of controlling the operation of the imaging system 11 in accordance with imaging condition including the slice condition set by the slice condition final setting section 65d, to thereby execute a main imaging of the slab area at the plurality of imaging positions set by the imaging position setting unit 62.

Figure 8:
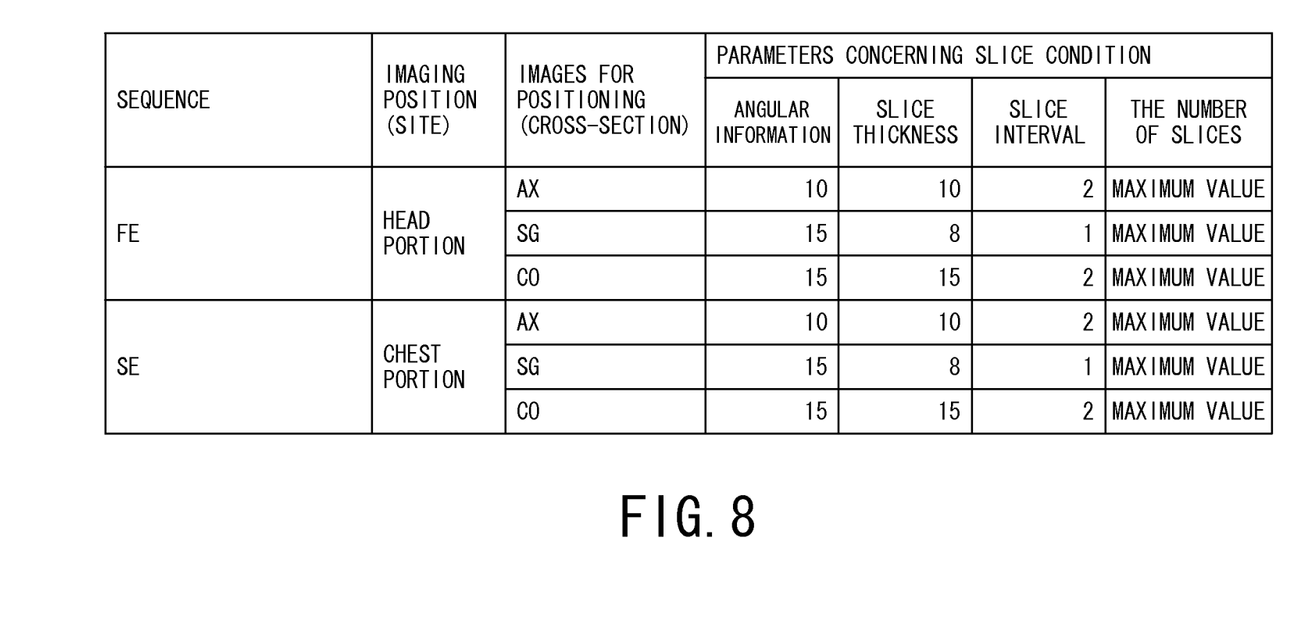
FIG. 8 is a table showing information for slice condition setting for setting a slice condition.

FIG. 8 is a table showing information for slice condition setting for setting a slice condition. FIG. 8 shows a modified example of the information for slice condition setting shown in FIG. 6.

FIG. 8 shows the information for slice condition setting indicating recommended values of a plurality of parameters concerning the slice condition, for example, angular information, a slice thickness, a slice interval, and the number of slices, which are given for each sequence, for each imaging position, and for each cross-section of the three orthogonal cross-sectional images. Note that the information for slice condition setting may contain the recommended values of the parameters at least for each imaging position.

For example, it is discussed in FIG. 8 that the sagittal image is used as the image for positioning in the case of imaging a head portion according to an FE method. In order to enable the slice areas to fall within the slab area, the number of slices needs to be set to such a maximum value that enables the slice areas to fall within the slab area without changing the temporary set values of the slice thickness and the slice interval set by the slice condition temporary setting section 65b. In this case, the temporary set value of the number of slices set by the slice condition temporary setting section 65b is ignored, and hence the slice condition temporary setting section 65b does not need to temporarily set the value of the number of slices. Note that the information for slice condition setting shown in FIG. 8 indicates that the number of slices is set to such a maximum value that enables the slice areas to fall within the slab area, but the present embodiment is not limited thereto. The information for slice condition setting may indicate that the slice thickness or the slice interval is set to such a minimum value or set value (for example, 1 or 0) that enables the slice areas to fall within the slab area.

Figure 9:
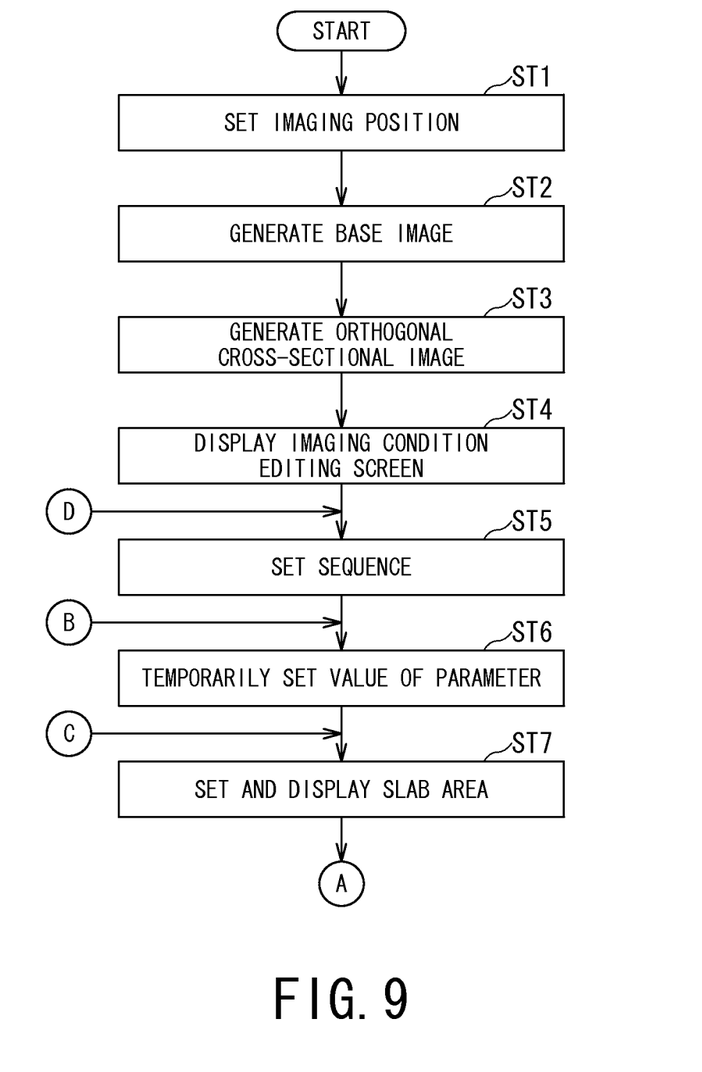
FIG. 9 is a flow chart showing an operation of the MRI apparatus according to the first embodiment.
Figure 10:
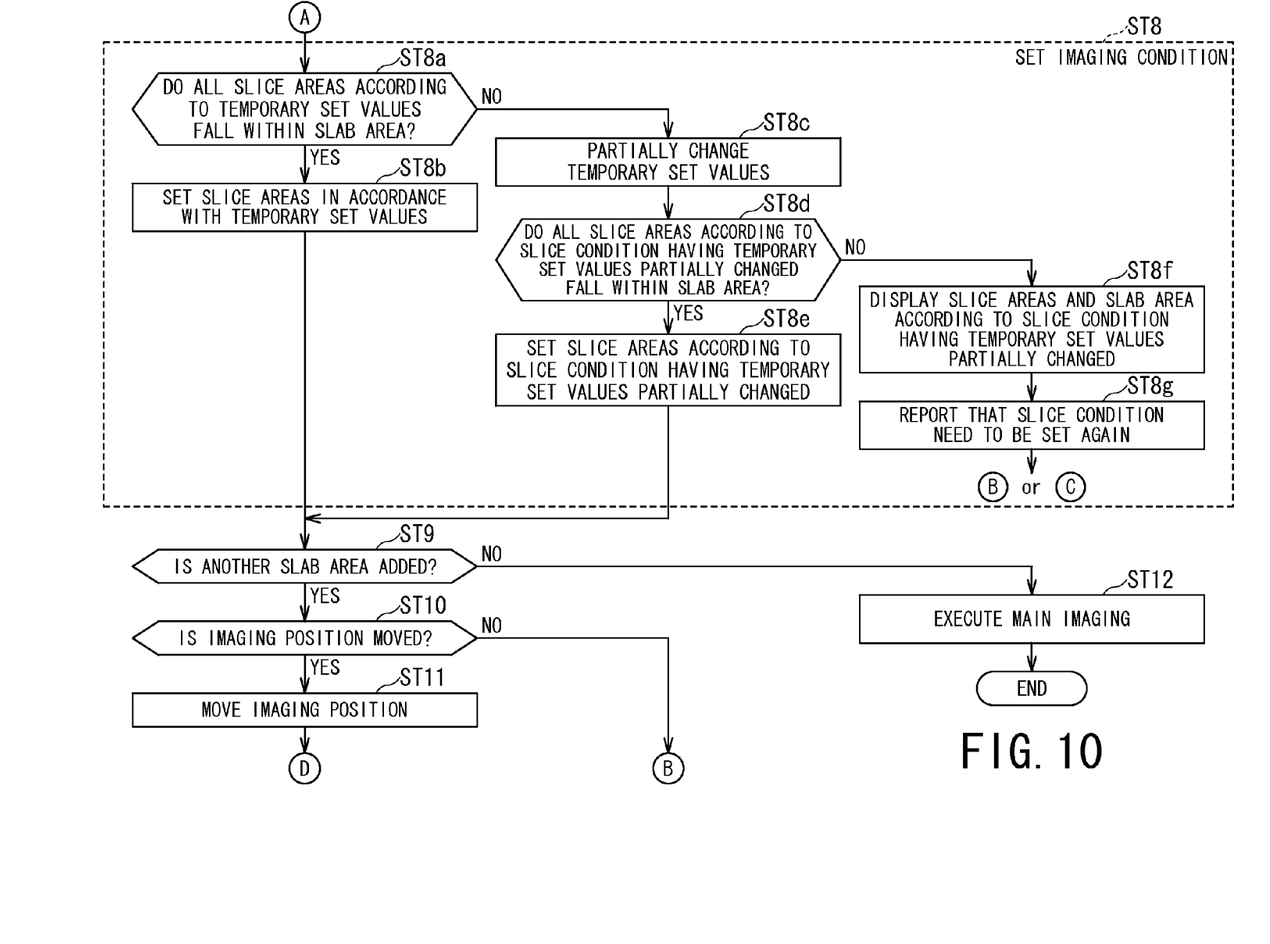
FIG. 10 is a flow chart showing an operation of the MRI apparatus according to the first embodiment.

Next, an operation of the MRI apparatus 10 according to the first embodiment is described with reference to flow charts shown in FIG. 9 and FIG. 10.

First, the MRI apparatus 10 sets one or more imaging positions (sites) concerning the object P (Step ST1). As described with reference to FIG. 3, the MRI apparatus 10 sets the imaging position(s) on the basis of: a coil element that receives NMR signals, among the receiver coils 28a to 28e, the coil element being set on the basis of an input signal that is inputted by the operator using the input device 36; and the entering direction of the object into the gantry. Description is given below of the case where the MRI apparatus 10 sets a plurality of imaging positions concerning the object P in Step ST1.

Subsequently, the MRI apparatus 10 controls the operation of the imaging system 11 in accordance with an imaging condition for a preliminary imaging (which is an imaging for setting parameters of the imaging condition for a main imaging) prior to the main imaging, and thus executing imagings for setting the respective slice areas at the plurality of imaging positions set in Step ST1, to thereby generate respective base images which are cross-sectional images (Step ST2). The MRI apparatus 10 generates orthogonal cross-sectional images taken along two cross-sections orthogonal to each base image, on the basis of the base image that is generated in Step ST2 for each imaging position (Step ST3). The MRI apparatus 10 causes the display device 35 to display the imaging condition editing screen including a sagittal image, a coronal image, and an axial image serving as the images for positioning concerning a first imaging position among the plurality of imaging positions generated in Steps ST2 and ST3 (Step ST4).

The MRI apparatus 10 sets a sequence of a main imaging concerning the first imaging position, included in an imaging condition, on the basis of an input signal that is inputted by the operator using the input device 36 on the imaging condition editing screen (Step ST5). The MRI apparatus 10 temporarily sets values of parameters concerning the slice condition concerning the first imaging position, included in the imaging condition, on the basis of an input signal that is inputted by the operator using the input device 36 on the imaging condition editing screen (Step ST6). The MRI apparatus 10 displays the input signal from the input device 36 on the imaging condition editing screen.

The MRI apparatus 10 sets angular information in the slice length direction of a slice area, which is a parameter concerning the slice condition of the slice area, on the basis of: the information for slice condition setting (shown in FIG. 6) stored in the storage 34; and the imaging positions set in Step ST1. Then, the MRI apparatus 10 sets a rectangular slab area on the image for positioning, on the basis of: an input signal that is inputted by the operator using the input device 36; and the set angular information, and displays the set slab area on the imaging condition editing screen (Step ST7). The setting of the slab area in Step ST7 is described above with reference to FIG. 4.

The MRI apparatus 10 sets rectangular slice areas in the slab area set in Step ST7, on the basis of: the temporary set values of the parameters set in Step ST6; and the set angular information (Step ST8). The MRI apparatus 10 determines whether or not all the slice areas according to the temporary set values of the parameters set in Step ST6 fall within the slab area (Step ST8a). If YES in the determination of Step ST8a, that is, in the case where it is determined that all the slice areas fall within the slab area as shown in FIG. 5, the MRI apparatus 10 finally sets the temporary set values of the parameters set in Step ST6, and sets the slice areas in accordance with the temporary set values of the parameters (Step ST8b).

On the other hand, if NO in the determination of Step ST8a, that is, in the case where it is determined that at least one slice area is not able to fall within the slab area as shown in FIG. 7A, the MRI apparatus 10 partially changes the temporary set values of the parameters set in Step ST6, in accordance with the information for slice condition setting (described with reference to FIG. 6) stored in the storage 34 (Step ST8c). The change of the slice condition in Step ST8c is described above with reference to FIGS. 7A and 7B.

Subsequently, the MRI apparatus 10 determines whether or not all the slice areas according to the slice condition having the temporary set values partially changed in Step ST8c fall within the slab area (Step ST8d). If YES in the determination of Step ST8d, that is, in the case where all the slice areas fall within the slab area as shown in FIG. 7B, the MRI apparatus 10 finally sets the slice condition having the temporary set values partially changed in Step ST8c, and sets the slice areas in accordance with the slice condition having the temporary set values partially changed (Step ST8e).

If NO in the determination of Step ST8d, that is, in the case where it is determined that at least one slice area is not able to fall within the slab area, the MRI apparatus 10 displays: all the slice areas according to the slice condition having the temporary set values partially changed in Step ST8c; and the slab area set in Step ST7, on the imaging condition editing screen (Step ST8f). Subsequently, the MRI apparatus 10 reports, to the operator, that the slice condition need to be temporarily set again (Step ST6) or that the slab area needs to be set again (Step ST7) (Step ST8g). Alternatively, instead of Steps ST8f and ST8g, the MRI apparatus 10 may automatically change the slab area such that all the slice areas fall within the slab area, and then may go to Step ST9. The report in Step ST8g to the effect that the slice condition need to be temporarily set again or that the slab area needs to be set again may be made by changing a display mode (color and the like) of the slice areas displayed in Step ST8f to be more clearly visible or by issuing a voice announcement.

The display made in Step ST8f enables the operator to visually check matching between the set slab area and the slice areas according to the temporary set values of the parameters.

Subsequently, the MRI apparatus 10 determines whether or not to add another slab area, on the basis of an input signal that is inputted by the operator using the input device 36 on the imaging condition editing screen (Step ST9). If YES in the determination of Step ST9, that is, in the case where it is determined that another slab area is added, the MRI apparatus 10 determines whether or not to switch from the first imaging position to a second imaging position included in the plurality of imaging positions set in Step ST1, on the basis of an input signal that is inputted by the operator using the input device 36 (Step ST10). If YES in the determination of Step ST10, that is, in the case where it is determined that the imaging position is switched, the MRI apparatus 10 switches the display of the image for positioning on the imaging condition editing screen to an image for positioning concerning the second imaging position, sets the second imaging position regarding the image for positioning after the switching (Step ST11), and returns to Step ST5.

On the other hand, if NO in the determination of Step ST10, that is, in the case where it is determined that the imaging position is not switched, in other words, in the case where another slab area is newly added to the same first imaging position, the MRI apparatus 10 temporarily sets the slice condition again, on the basis of an input signal that is inputted by the operator using the input device 36 on the imaging condition editing screen (Step ST6).

If NO in the determination of Step ST9, that is, in the case where it is determined that another slab area is not added, the MRI apparatus 10 controls the operation of the imaging system 11 in accordance with an imaging condition including the slice areas finally set in Steps ST8b and ST8e, to thereby execute a main imaging of the slab area at the plurality of imaging positions set in Step ST1 (Step ST12).

According to the MRI apparatus 10 of the first embodiment, because a change priority parameter is set as a predetermined parameter of a slice condition, the operator is able to set slice conditions different for each slab area through an easier operation, in the case where different slab areas are set at one imaging position or in the case where slab areas are respectively set at a plurality of imaging positions. In addition, according to the MRI apparatus 10 of the first embodiment, because matching between slice areas according to a slice condition and a slab area is displayed for each slab area, the operator is able to visually check, for each slab area, the matching between the slice areas according to the slice condition and the slab area.

Moreover, according to the MRI apparatus 10 of the first embodiment, in the case where a plurality of slice areas according to a slice condition are not able to fall within a slab area set on an image for positioning, temporary set values of parameters concerning the slice condition are partially changed automatically in order of priority, and hence a burden put on the operator is able to be reduced. It is preferable that the order of priority be set for each imaging position.

Second Embodiment

A schematic diagram of a hardware configuration of an MRI apparatus 10A of a second embodiment is the same as the schematic diagram of the hardware configuration of the MRI apparatus 10 of the first embodiment shown in FIG. 1, and hence description thereof is omitted.

Figure 11:
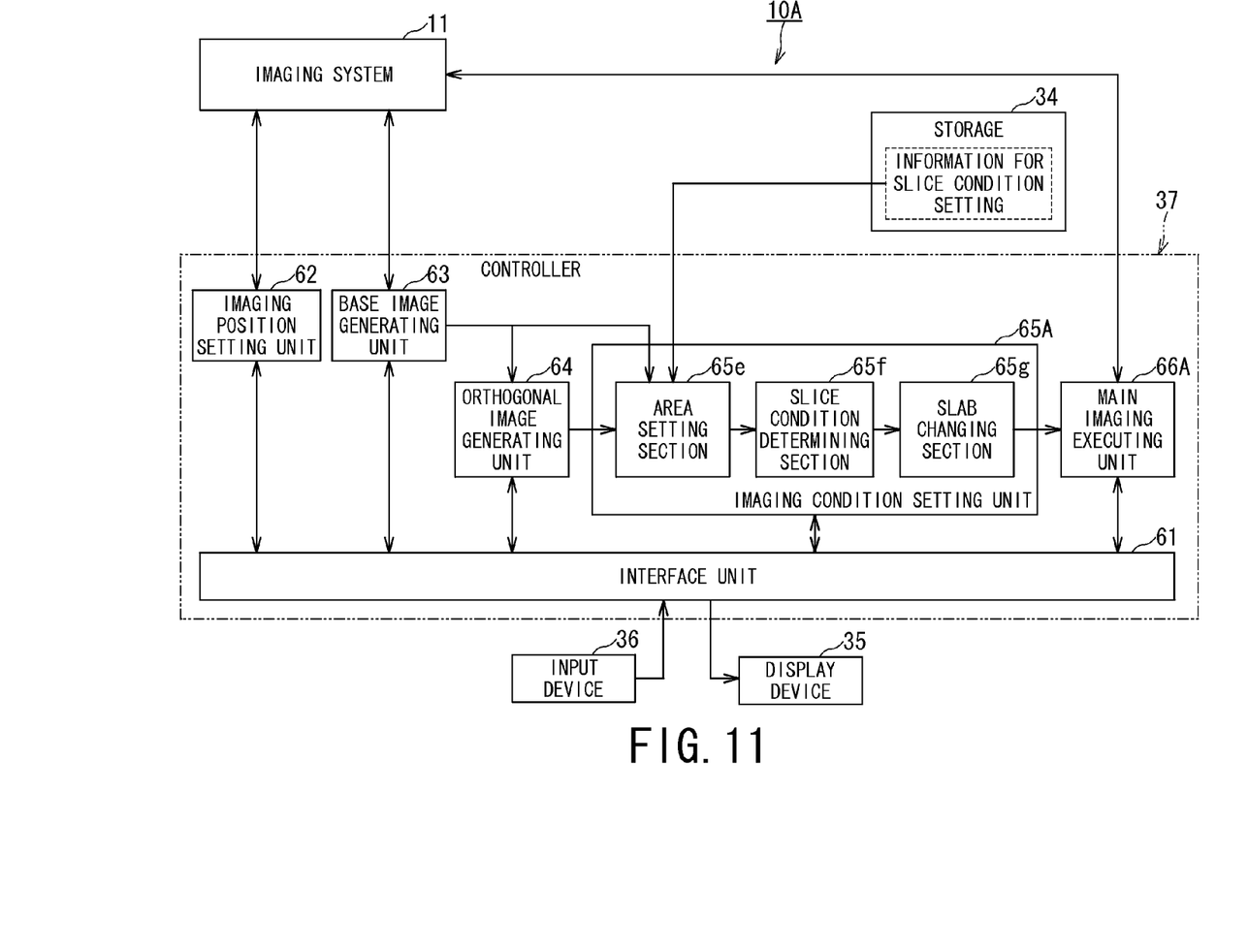
FIG. 11 is a block diagram showing a function of an MRI apparatus of a second embodiment.

FIG. 11 is a block diagram showing a function of the MRI apparatus 10A of the second embodiment.

As shown in FIG. 11, when the CPU of the controller 37 executes a program, the MRI apparatus 10A functions as the interface unit 61, the imaging position setting unit 62, the base image generating unit 63, the orthogonal image generating unit 64, an imaging condition setting unit 65A, and a main imaging executing unit 66A. Note that description is given below assuming that the components 61 to 66A of the MRI apparatus 10A are caused to function in the form of software, but a part or the entirety of the components 61 to 66A may be provided as a circuit in the MRI apparatus 10A.

Note that, in the MRI apparatus 10A of the second embodiment shown in FIG. 11, the same components as those in the MRI apparatus 10 of the first embodiment shown in FIG. 2 are denoted by the same reference signs, and description thereof is omitted.

The imaging condition setting unit 65A includes an area setting section 65e, a slice condition determining section 65f, and a slab changing section 65g. The imaging condition setting unit 65A edits an imaging condition on the imaging condition editing screen.

The area setting section 65e has a function of setting a slab area and slice areas on the basis of recommended values corresponding to the imaging position(s) set by the imaging position setting unit 62, the recommended values being contained in the information for slice condition setting (shown in FIG. 6) stored in the storage 34. The slab area and the slice areas set by the area setting section 65e are displayed on the image for positioning with the intermediation of the interface unit 61.

The slice condition determining section 65f has a function of determining a slice condition on the basis of the slice areas set by the area setting section 65e.

The main imaging executing unit 66A has a function of controlling the operation of the imaging system 11 in accordance with an imaging condition including the slice condition determined by the imaging condition setting unit 65A, to thereby execute main imaging of the slab area at the plurality of imaging positions set by the imaging position setting unit 62.

The slab changing section 65g has a function of changing a slab area on the image for positioning. In this case, the main imaging executing unit 66A executes imaging of the changed slab area, in accordance with the slice condition determined by the slice condition determining section 65f.

Further, the area setting section 65e preferentially changes, if the slab changing section 65g changes the slab area on the image for positioning, a change priority parameter corresponding to the imaging position set by the imaging position setting unit 62, from its recommended value to another value, to thereby change the slice areas, the change priority parameter being contained in the information for slice condition setting (shown in FIG. 6) stored in the storage 34. In this case, the slice condition determining section 65f determines the slice condition on the basis of the changed slice areas.

For example, it is discussed in FIG. 6 that the sagittal image is used as the image for positioning in the case of imaging of a head portion according to an FE method. If the slab changing section 65g enlarges the slab area on the image for positioning, the area setting section 65e preferentially changes the slice thickness as the change priority parameter from its recommended value "8" to a larger value. Then, for example, it is discussed in FIG. 6 that the sagittal image is used as the image for positioning in the case of imaging of a chest portion according to an SE method. The change priority parameter does not exist for the area setting section 65e. In this case, even if the slab changing section 65g enlarges the slab area on the image for positioning, the area setting section 65e may keep all the parameters at their respective recommended values.

According to the MRI apparatus 10A of the second embodiment, because a change priority parameter is set as a predetermined parameter of a slice condition, the operator is able to set slice conditions different for each slab area through an easier operation, in the case where different slab areas are set at one imaging position or in the case where slab areas are respectively set at a plurality of imaging positions. In addition, according to the MRI apparatus 10A of the second embodiment, because matching between slice areas according to a slice condition and a slab area is displayed for each slab area, the operator is able to visually check, for each slab area, the matching between the slice areas according to the slice condition and the slab area.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
MRI system components including static and gradient magnetic field generators, at least one radio frequency (RF) coil, an RF transmitter, an RF receiver, at least one computer and associated storage configured to store recommended values of a slice condition parameter corresponding to respective different classified imaging positions;
said at least one computer being configured to
image an object on a predetermined imaging position, and to generate an image for positioning;
set a slab area and a slice area on a basis of a recommended value, read from said storage corresponding to a predetermined imaging position of the classified imaging positions, and display the set slab area and the set slice area on the image for positioning;
determine the slice condition on a basis of the slice area; and
execute an imaging of the slab area in accordance with the determined slice condition.

2. The magnetic resonance imaging apparatus according to claim 1, wherein said at least one computer is further configured to
change the slab area on the image for positioning, and execute imaging on the changed slab area in accordance with the determined slice condition.

3. The magnetic resonance imaging apparatus according to claim 2, wherein
said storage is configured to store recommended values for first and second slice condition parameters and for change priority parameters corresponding to the respective different classified imaging positions, the change priority parameters each indicating one of the first and second slice condition parameters,
said at least one computer also being configured to preferentially change, if the slab area is changed on the image for positioning, a recommended value, read from the storage in the predetermined imaging position and in a change priority parameter corresponding to the predetermined imaging position, and thereby changing the slice area, and
determine the slice condition on a basis of the changed slice area.

4. A magnetic resonance imaging apparatus comprising:
MRI system components including static and gradient magnetic field generators, at least one radio frequency (RF) coil, an RF transmitter, an RF receiver, at least one computer and associated storage configured to store change priority parameters corresponding to respective different classified imaging positions, the change priority parameters each indicating one of first and second slice condition parameters, said computer being configured to image an object on a predetermined imaging position, and to generate an image for positioning;

temporarily set a value of the first slice condition parameter and a value of the second slice condition parameter;

set a slab area on the image for positioning;

change, in a case where a plurality of slice areas according to the respective first and second slice condition parameters are placed and where the plurality of slice areas do not fall within the slab area, a temporary set value in the predetermined imaging position and in a change priority parameter corresponding to the predetermined imaging position, such that the plurality of slice areas fall within the slab area, thereby setting the partially changed slice condition to a finally set slice condition; and execute an imaging of the slab area in accordance with the finally set slice condition.

5. The magnetic resonance imaging apparatus according to claim 4, wherein the computer is further configured to
set the predetermined imaging position on a basis of (a) a coil element that receives a signal, among coil elements included in a receiver coil and (b) an entering direction of the object into a gantry.

6. The magnetic resonance imaging apparatus according to claim 4, wherein the computer is further configured to
set the predetermined imaging position on a basis of an input by an operator.

7. The magnetic resonance imaging apparatus according to claim 4, wherein the computer is further configured to
report to an operator, in a case where the plurality of slice areas do not fall within the slab area even after a change of a parameter corresponding to the predetermined imaging position, that the slice condition and/or the slab area needs to be changed.

8. The magnetic resonance imaging apparatus according to claim 4, wherein
two points are specified on the image for positioning on a basis of an input by an operator, and the slab area is set on a basis of the two points and an oblique angle stored for each imaging position.

9. The magnetic resonance imaging apparatus according to claim 4, wherein the plurality of parameters are at least two of: an oblique angle, a slice thickness, a slice interval, and a number of slices.

10. A magnetic resonance imaging apparatus comprising:
MRI system components including static and gradient magnetic field generators, at least one radio frequency (RF) coil an RF transmitter, an RF receiver, at least one computer and storage configured to store a change priority parameter as a number of slices, the change priority parameter indicating one of a plurality of slice condition parameters;

said at least one computer being configured to image an object at a predetermined imaging position, and generate an image for positioning;

temporarily set values in a plurality of parameters and in a plurality of imaging positions;

set a slab area on the image for positioning;

change, in a case where a plurality of slice areas according to the respective parameters are placed and where the plurality of slice areas do not fall within the slab area, a temporary set value of the number of slices read from storage, such that the plurality of slice areas fall within the slab area, thereby finally setting the slice condition; and execute an imaging of the slab area in accordance with the finally set slice condition.

* * * * *